United States Patent [19]

Stenman et al.

[11] Patent Number: 4,559,311

[45] Date of Patent: Dec. 17, 1985

[54] DIAGNOSTIC METHOD USING ONCOFETAL PEPTIDE AS A TUMOR MARKER

[76] Inventors: Ulf-Håkan Stenman, Heikelsvägen 10, SF-02700 Grankulla; Marja-Liisa Huhtala, Mörtnäsvägen 15 E, SF-00210 Helsingfors 21, both of Finland

[21] Appl. No.: 400,384

[22] Filed: Jul. 21, 1982

[30] Foreign Application Priority Data

Aug. 27, 1981 [SE] Sweden ................................. 8105071

[51] Int. Cl.[4] ...................... G01N 33/54; G01N 33/58; A61K 39/00; C07C 103/52
[52] U.S. Cl. ............................... 436/542; 260/112 R; 260/112.5 R; 436/543; 436/545; 436/811; 436/813; 436/815; 436/547
[58] Field of Search ..................... 424/1.1, 9; 436/542–545, 804, 813; 260/112 R, 112.5 R

[56] References Cited

U.S. PATENT DOCUMENTS

| | | | |
|---|---|---|---|
| 3,663,684 | 5/1972 | Freedman | 424/1 |
| 4,140,753 | 2/1979 | Edgington et al. | 436/804 |
| 4,331,647 | 5/1982 | Goldenberg | 424/1.1 |
| 4,361,544 | 11/1982 | Goldenberg | 424/1.1 |

OTHER PUBLICATIONS

Rees et al., J. Nat'l Cancer Inst., 67 (1981) 557–61.
Irie et al., Cancer Res., 36 (1976) 3510–17.
Fritsché et al., Nature, vol. 258 (Dec. 1975) 734–737.
Goldenberg et al., Cancer Res., 38 (1978) 1246–1249.
Irie et al., J. Nat. Cancer Inst., 63 (1979) 367–373.
Cauchi et al., Chem. Abstracts, 96 (1982) #50442y.
Bartelt, Diana C., et al., Archives of Biochemistry and Biophysics, vol. 179, (1977) pp. 189–199.
Eddeland, Allan, et al., Hoppe-Seyler's Z. Physiol, Chem., vol. 359, (Jun. 1978), pp. 671–675.
Kitahara, Takeshi, et al., Clinica Chimica Acta, vol. 103 (1980), pp. 135–143.

*Primary Examiner*—Christine M. Nucker
*Attorney, Agent, or Firm*—Fisher, Christen & Sabol

[57] ABSTRACT

Method for the diagnosis of cancer tumors which comprises determining the concentration of oncofetal urine peptide in the blood serum or the urine of the patient. The oncofetal urine peptide is immunochemically identifiable by means of an antiserum which is produced by the immunization of purified oncofetal urine peptide. The purification method has the following steps:

(a) concentrating urine peptides from cancer patients by means of dialyzation and lyophilization;
(b) separating the urine peptides having a molecular weight of 4,000 to 10,000 by means of gel filtration to achieve a peptide fraction;
(c) concentrating of the peptide fraction through lyophilization;
(d) subjecting the peptide fraction to ion exchange chromatography by using SP-Sephadex, gradient elution at pH 4 to 5, ion strength 0.1 to 0.5 mol/l;
(e) subjecting the treated peptide fraction to high Pressure Liquid Chromatography using a reverse phase column and eluation in a gradient containing phosphate buffer 10 mmol/l pH 6.2, and acetonitrile 10 to 45 percent;
(f) subjecting the treated peptide fraction to gel filtration by means of Sephadex G-50 in acetic acid solution 0.1 mol/l; and
(g) lyophilyzing the treated peptide fraction.

2 Claims, No Drawings

DIAGNOSTIC METHOD USING ONCOFETAL PEPTIDE AS A TUMOR MARKER

BACKGROUND OF THE INVENTION

1. Field of the Invention

The present invention refers to a method for radioactive marking of an oncofetal urine peptide and the use of the peptide as a cancer diagnostics, preferably in gynecological cancer.

2. Prior Art

The diagnostics of cancer patients is difficult as the disease does not usually give any symptoms in its initial state. In many cases the disease is discovered only in a state when the cancer tumour is so big that the disease is incurable or difficult to cure. In this state the tumour also often has sent out metastases. If the disease is discovered in an early state it is however often possible to cure it completely. For this reason one has been looking for tumour markers, i.e. substances produced by the tumour or being generated as a result of the tumour disease which could be used for diagnostics of the disease. Tumour markers of this kind are for instance alphafetoprotein (AFP) and carcinoembryonal antigen (CEA). For a closer description of CEA is referred for instance to the U.S. Pat. No. 3,663,684 (Freedman, S.O.). AFP and CEA can be detected in serum samples and increased concentrations indicate certain tumour diseases. AFP is a relatively sensitive marker for liver and testis cancer, but is not useful in other tumours. CEA is increased in a number of tumour disease but the specificity of the determination is relatively low. Therefore, CEA-determinations are mainly used for monitoring patients with increased values. For choricarcinon there is a very specific marker, koriongonadotropin (hCG) which is also produced in normal placenta. By determining the hCG recurrences can be diagnosed in a very early state. Because of this, the treatment of choriocarcinon is nowadays very successful.

Good tumour markers thus have a very high value but for most tumours no markers exist or exist only in a certain percentage or alternatively in a very late state of the disease.

BROAD DESCRIPTION OF THE INVENTION

It is an object of the present invention to provide a method of using a marker for tumours which cannot be diagnosed by means of other markers. The marker used also gives additional information in cases where other markers give a positive but not a conclusive result. The marker could be used for a primary diagnostics of tumours as well as for monitoring of patients who have been treated for tumours, especially malignant tumours. By means of determining at certain intervals the concentration of the marker used which in below is called OFP-1 (oncofetal peptide No. 1) it is possible to determine whether the tumour treatment has been successful. If the tumour is eliminated the concentration of the marker is decreased. If the concentration raises again this indicates a growth of the tumour.

The invention furthermore concerns a method for radioactive marking of the peptide and the diagnostic use of the peptide as a tumour marker.

The present invention involves a method for the diagnosis of cancer tumors. The method includes determining the concentration of oncofetal urine peptide in the blood serum or the urine of the patient. The oncofetal urine peptide is immunochemically identifiable by means of an antiserum which is produced by the immunization of the purified oncofetal urine peptide. The purification method has the following steps:

(a) concentrating urine peptides from cancer patients by means of dialyzation and lyophilization;
(b) separating the urine peptides having a molecular weight of 4,000 to 10,000 by means of gel filtration to achieve a peptide fraction;
(c) concentrating of the peptide fraction through lyophilization;
(d) subjecting the peptide fraction to ion exchange chromatography by using SP-Sephadex, gradient elution at pH 4 to 5, ion strength 0.1 to 0.5 mol/l;
(e) subjecting the treated peptide fraction to High Pressure Liquid Chromatography using a reverse phase column and eluation in a gradient containing phosphate buffer 10 mmol/l pH 6.2, and acetonitrile 10 to 45 percent,
(f) subjecting the treated peptide fraction to gel filtration by means of Sephadex G-50 in acetic acid solution 0.1 mol/l; and
(g) lyophilyzing the treated peptide fraction.

The cancer tumor particularly is derived from gynecological cancer. The determination can be achieved by means of an immunochemical method. The immunochemical method can be radioimmunoassy (RIA) using the oncofetal urine peptide radioactively marked with iodine 125.

DETAILED DESCRIPTION OF THE INVENTION

Method for Producing the Peptide OFP-1

OFP-1 has been produced in the following way. Five liters of urine from a patient suffering from ovarian cancer is dialyzed towards $NH_4HCO_3$ buffer 0.1 mol/l pH 8.5 and is concentrated. The concentrated urine is fractionated by gel filtration in Sephadex G-75 in the above defined buffer. The fraction having the molecular size 4,000–10,000 dalton (Fraction 1) is lyophilized and dissolved in Na-acetate buffer, 100 $\mu$mol/l pH 4, an SP-Sephadex-column is equilibrated with the same buffer. The fraction 1 is applied to the SP-Sephadex column which is then eluted with a gradient consisting of equal parts Na-acetate buffer, the first having a concentration of 0.1 mol/l pH 4.0, the second having a concentration of 0.5 mol/l, pH 4.5. OFP-1 is eluted at a buffer concentration of 0.15–0.30 mol/l (Fraction 2). Simultaneously, the peptide OFP-1 is fractionated in 3–5 subcomponents. Fraction 2 is dialyzed towards distilled water and is lyophilized. It is then dissolved in 2 ml Na-phosphate-buffer, 0.01 mol/l, pH 6.2. Subsequent purification is made through High Pressure Liquid Chromatography (HPLC) with a reverse phase column (Hewlett Packard RP-8). Fraction 2 is injected in 1–2 ml volume. OFP-1 is eluted with a gradient consisting of two solutions, A and B. The solution A consists of the above-mentioned Na-phosphate buffer, solution B contains 45 parts of acetonitrile and 55 parts of the solution A. When injecting the sample the column is eluted with the solution A/B in a ratio of 90/10, flow velocity 1.4 ml/min. Immediately after the injection a linear gradient elution is initiated which after 20 minutes ends up by containing 100 percent of solution B. OFP-1 is eluted after 10–13 minutes and can be detected as a well defined peak in the chromatogram through its light absorption at 280 nm. A number of smaller peaks containing OFP-1 are also present in most samples. The exact time of retention for OFP-1 varies in dependence of variations of properties of the RP-8 column. The fraction containing OFP-1 is lyophilized (Fraction 3). The lyophilized fraction 3 is dissolved in acetic acid solution, 0.1 mol/l, and the peptide is finally purified through a gel filtration in Sephadex G-50 in acetic acid solution, 0.1 mol/l. OFP-1 can be detected by means of its light absorption at 280 nm wavelength (fraction 4). OFP is eluted as a peptide having a molecular weight of 7,000. Fraction 4 is lyofilized. The amount OFP in fraction 4 is determined through weighing.

Method for producing antiserum specifically for the peptide OFP-1

Antiserum directed towards OFP-1 is produced by means of immunisation by purified OFP-1. Fifty μg OFP-1 were dissolved in 0.5 ml 0.9% NaCl-solution. This solution was mixed with a 0.5 ml "Freunds complete adjuvant", and was injected subcutant at 5–10 different locations in a rabbit. The immunisation was repeated three times at intervals of three weeks. Two weeks after the last immunisation blood was taken from the rabbit and serum was separated. The antiserum is analyzed by means of immunodiffusion in an agar gel according to the Ouchterlony technique. Purified OFP-1 in concentrations between 5 and 100 μg/ml form only one precipitation line. When urine containing large amounts OFP-1 are tested this also gives rise to only one precipitation line. In immunodiffusion OFP-1 in urine and purified OFP-1 show immunological identity. Serum and urine from healthy persons will not generate a precipitation line at immunodiffusion.

Method for marking of OFP-1 by using radioactive iodine 125

OFP-1 is marked with radioactive iodine according to Hunter's and Greenwood's method. Thus, 0.5 mCi Na$^{125}$J in a volume of 5 μl and 10 μl chloramine-T (4 g/l) is added to a solution of 5 μg OFP-1 in a 25 μl phosphate buffer, 0.5 mol/l pH 7.5. The solution is mixed and after 10–15 seconds 50 μl $Na_2S_2O_5$ solvent is added (3 g/l). To this solution another 100 μl NaJ-solution is added (10 g/l), whereafter the iodinated peptide is separated from excess of iodine by means of gel filtration in Sephadex G-25. The radioactive peptide is collected in 1 ml fractions in glass tubes containing 0.5 ml of an NaCl buffer containing 0.1% bovine serum albumin. Iodinated OFP-1 is stored at −20° C.

Determination of OFP-1 by Radioimmunoassay (RIA)

For dissolving antiserum, OFP-1 standard and iodinated OFP-1 a buffer containing Na-phosphate 10 mmol/l, pH 7.4, NaCl 0.15 mol/l, bovine serum albumin 1 g/l and Na-azide 0.2 g/l (RIA-buffer) is used. The antiserum is dissolved so that it binds 30–40% of an amount iodine marked OFP-1 containing 10,000–15,000 cpm radioactivity, when these are incubated in the volume ratios 0.1 ml antiserum, 0.1 ml iodinated OFP-1 and 0.1 ml buffer. This antibody bound fraction is separated after 12–16 hours by adding 0.1 ml antiserum directed towards rabbit-immunoglobulin G (secondary antibody). After about 1 hour the precipitate formed is separated by means of centrifugation during 15 minutes at 2500–3000 rpm corresponding to a centrifugal force of about 1500 g. The supernatant is decanted or aspirated and the radioactivity of the precipitate is measured in a gamma counter.

When determining OFP-1 in urine, serum or tissue extract the above mentioned amounts (0.1 ml) antiserum and radioactive OFP-1 and 0.1 ml sample is used or use is made of standards containing predetermined amounts of OFP-1. The OFP-1 concentration of the standards are determined by the affinity of the antiserum 7 standards having concentrations of 1.6 to 100 μg/l are usually suitable. Urine- and serum samples are dissolved with RIA-buffer tenfold before the determination. Incubation and separation of the bound fraction is made in accordance with the above description. On the basis of the radioactivity in the standard samples a standard curve is made. The OFP-1 concentration of the samples are then determined by means of the standard curve.

The concentration is serum of healthy persons of the peptide produced as described above is 5–20 μg/l and in urine 6–50 μg/l. 95% of the values for healthy persons would fall within these limits. Chemically OFP-1 is thus a peptide with an approximate molecular weight of 7000 dalton. It is microheterogeneous in isoelectric focusing having an isoelectric point in the pH-range 5–6. The peptide does not contain any carbohydrates and its approximate aminoacid composition is defined as follows:

TABLE 1

The amino acid configuration of the peptide OFP-1. The peptide has been hydrolyzed in 6 mol/l HCl for 20 hours. The values are based on the fact that the molecular weight of the peptide is about 6,500–7,000.

| | amino acids/molecule |
|---|---|
| Lysine | 5.0 |
| Arginine | 3.3 |
| Asparagine acid/asparagine | 4.7 |
| Treonine | 4.4 |
| Serine | 3.1 |
| Glutamine acid/glutamine | 9.0 |
| Proline | 1.1 |
| Glycine | 6.7 |
| Alanine | 1.5 |
| Valine | 2.4 |
| Metionine | 2.7 |
| Isoleucine | 4.5 |
| Leucine | 2.9 |
| Tyrosine | 2.2 |
| Fenylalanine | 1.3 |
| Histidine | 0 |
| Tryptofan | ? |
| Cysteine | ? |

The N-terminal amino acid sequence of the peptide OFP-1 has been determined by so called Edman degradation. The 1 0 first amino acids are as follows: ASP-SER-LEU-GLY-X-GLU-ALA-LYS-X-TYR-.

Determination of OFP-1 is used for diagnostics of patients with different kinds of cancer which gives rise to an increased concentration of the peptide. The determination is carried out with immunochemical techniques applied on samples of urine, blood serum or other body fluids. The determination is used for primary diagnostics and for monitoring of patients, for instance in connection with or after treatment. The determination can also be used for monitoring patients which cannot be treated. In 15 patients with ovarian cancer the urine concentrations were 80–12,000 μg/l, whereas a patient recently subject to treatment has a normal concentration. Out of 30 patients with other kinds of cancer, 20 had values above the reference values for healthy persons.

Determination of OFP-1 could alternatively be carried out with other immunochemical methods than the above described RIA-method. It is thus possible to use for instance enzyme immunoassay, fluoroimmunoassay, nephelometry, turbidimetry, rocket electrophoresis or radial immunodiffusion.

As the concentration of the peptide OFP-1 in urine is also dependent on the functioning of the kidneys, determinations of OFP-1 could be used for evaluating the kidney function of patients having a defected kidney function. In this respect, OFP-1 reacts in the same manner as the protein beta-2-microglobuline. Because of the affection of the kidney function of the OFP-1 concentration this function should be considered in evaluating the concentration. It should finally be mentioned that OFP-1 also can be isolated from amniotic fluid or tumour extract.

We claim:

1. Method for purification of an oncofetal urine peptide comprising the following steps:
    (a) concentrating urine peptides from at least one cancer patient by means of dialyzation and lyophilization;
    (b) separating the urine peptides having a molecular weight of 4,000 to 10,000 by means of gel filtration to achieve a peptide fraction;
    (c) concentrating of the peptide fraction through lyophilization;
    (d) subjecting the peptide fraction to ion exchange chromatography using gradient elution at pH 4 to 5, and ion strength of 0.1 to 0.5 mol/l;
    (e) subjecting the treated peptide fraction to High Pressure Liquid Chromatography using a reverse phase column and eluation in a gradient containing phosphate buffer 10 mmol/l ph 6.2, and acetonitrile 10 to 45 percent;
    (f) subjecting the treated peptide fraction to gel filtration assisted by acetic acid solution 0.1 mol/l; and
    (g) lyophilyzing the treated peptide fraction.

2. Method for the diagnosis of cancer tumors which comprises determining the concentration of oncofetal urine peptide in the blood serum or the urine of the patient, the oncofetal urine peptide having a molecular weight of about 6,500 as determined by gel chromatography and having a N-terminal amino acid sequence wherein the first ten amino acids are:

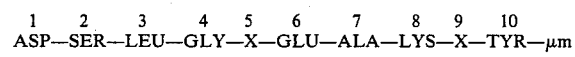

wherein X is an unidentified amino acid moiety.

* * * * *